United States Patent [19]

Buckler et al.

[11] Patent Number: 4,647,668

[45] Date of Patent: Mar. 3, 1987

[54] DISOPYRAMIDE PHENYL DERIVATIVES AND LABELED CONJUGATES

[75] Inventors: Robert T. Buckler, Edwardsburg, Mich.; Stephan G. Thompson, South Bend, Ind.

[73] Assignee: Miles Laboratories, Inc., Elkhart, Ind.

[21] Appl. No.: 736,100

[22] Filed: May 20, 1985

Related U.S. Application Data

[62] Division of Ser. No. 455,224, Jan. 3, 1983, abandoned.

[51] Int. Cl.$^4$ .................. C07D 213/56; C12N 9/96
[52] U.S. Cl. .................................. 546/333; 546/336; 435/7; 435/188
[58] Field of Search .................. 546/333, 336; 435/7, 435/188

[56] References Cited

U.S. PATENT DOCUMENTS 4,079,061 3/1978 Berkoff et al. .................. 546/333
4,288,553 9/1981 Singh et al. .................. 546/333

FOREIGN PATENT DOCUMENTS 37-11829 8/1962 Japan .
771814 6/1954 Sweden .

OTHER PUBLICATIONS

Karim et al., "Species Differences in the Biotransformation of a New Antiarrhythmia Agent: Disopyramide Phosphate", *J Pharmaceutical Science*, vol. 61(6), 1972, pp. 888–893.

*Primary Examiner*—Morton Foelak
*Assistant Examiner*—Garnette D. Draper
*Attorney, Agent, or Firm*—Daniel W. Collins; Andrew L. Klawitter

[57] ABSTRACT

Disopyramide immunogens, antibodies prepared therefrom, labeled conjugates, synthetic intermediates, and the use of such antibodies and labeled conjugates in immunoassays for determining disopyramide. The immunogens comprise disopyramide coupled by an ether linkage at a selected singular position on its phenyl ring to an immunogenic carrier material. Likewise, the labeled conjugates and synthetic intermediates are phenyl ether derivatives of disopyramide or precursors thereof. The antibody and labeled conjugates are particularly useful in homogeneous nonradioisotopic immunoassays for measuring disopyramide in biological fluids such as serum.

6 Claims, No Drawings

DISOPYRAMIDE PHENYL DERIVATIVES AND LABELED CONJUGATES

This is a division of application Ser. No. 455,224, filed Jan. 3, 1983, now abandoned.

BACKGROUND OF THE INVENTION

1. Field of the Invention

This invention relates to novel disopyramide derivatives pertaining to immunoassays for determining the drug in liquid media such as biological fluids. Such derivatives include immunogens used to stimulate production of antibodies to disopyramide in host animals by conventional techniques. Also provided are labeled disopyramide conjugates used as reagents, along with the antibodies, in particularly preferred immunoassays. Intermediates in the synthesis of the aforementioned immunogens and labeled conjugates are also provided.

Disopyramide [Merck Index, 9th ed., pp. 449 & 450 (1976)] is a cardiovascular drug of the formula:

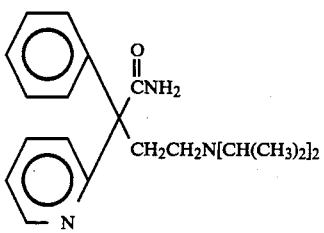

used to treat advanced coronary artery disease and to prevent specific ventricular rhythm disturbances including those following myocardial infarction. [J. Koch-Weser, New Engl. J. Med. 300: 957 (1979); G. Jennings, et al, Am. J. Cardiol. 46: 469 (1980)]. It is sold in the U.S. as the mono-phosphate salt under the tradename NORPACE® ("Physicians' Desk Reference", 36th ed., Medical Economics Co., Oradell, NJ, 1982, p. 1784).

Disopyramide also posseses anti-cholinergic properties, and the most common side effects of the drug are due to this aspect of its pharmacological activity. Patients with glaucoma or benign prostatis hypertrophy are at particular risk. Disopyramide can also induce many types of cardiac dysrhythmia, as well as depress myocardial contractility, and cardiac and arterial pressure. Such toxic effects are usually dose-related and are due to excessive concentrations of the drug in the plasma or myocardium [J. Koch-Weser, supra; E. G. Manolas, et al, Med. J. Aust. 20 (1979)].

Therapeutic plasma levels occur in a narrow concentration range of 2-4 micrograms/mL [P. Danilo and M. R. Rosen, Am. Heart J. 92: 532 (1976)]. The half-life of disopyramide in normal volunteers ranges from 3.4 to 10.8 hours. Such variations in half-life make measurement of plasma levels essential to ensure that the dosage is appropriate to maintain plasma levels within the therapeutic range, and to decrease the side effects associated with higher levels of the drug [K. Ilett, et al, J. Chromat. 154: 325 (1978)].

2. Description of the Prior Art

Several analytical methods have been developed for measuring blood levels of disopyramide and its principal metabolite. They include gas-liquid chromatography [A. Johnston and D. McHaffie, J. Chromat. 152: 501 (1978)], high performance liquid chromatography [P. -O. Lagerstrom and B. -A. Persson, J. Chromat. 149: 331 (1978)], thin layer chromatography [R. N. Gupta, et al, Anal. Chem. 51: 445 (1979)], enzyme-mediated immunoassay [A. Johnston and J. Hamer, Clin. Chem. 27: 353 (1981)], and differential-pulse polarography [J. F. Burmicz, et al, Analyst (London) 106: 802 (1981)].

The preparation of antibodies to disopyramide for use in immunoassays to determine the drug has been accomplished in the prior art by essentially two different approaches. One approach has been to couple the drug through its amide group to an appropriate carrier material [U.S. Pat. No. 4,288,553]. The second approach involves random nitration of the phenyl ring followed by conversion of the nitro groups to amino groups and conventional peptide condensation to the carrier molecule [Japanese Provisional Spec. No. 56-046,820 (Derwent No. 44742D/25)]. The immunogens resulting from the second approach are a mixture of ortho-, meta-, and para-coupled drug derivatives producing a particularly heterogeneous antibody population.

The state-of-the-art of preparing antibodies to haptens such as drugs is represented by Weinryb et al, Drug Metabolism Reviews 10: 271 (1979); Playfair et al, Br. Med. Bull. 30: 24 (1974); Broughton et al, Clin. Chem. 22: 726 (1976); and Butler, J. Immunol. Meth. 7: 1 (1976) and Parmacol. Rev. 29(2): 103 (1978). Labeled conjugates, comprising the analyte or a derivative or other analog thereof, coupled to a labeling susbstance are variously described in the literature, e.g., U.S. Pat. Nos. 4,279,992; 4,182,856; 4,259,233; and 4,292,425 wherein the label is the fluorogenic enzyme substrate β-galactosyl-umbelliferone.

SUMMARY OF THE INVENTION

The present invention uniquely provides reagents for use in disopyramide immunoassays involving the coupling to or derivatization of the drug by an ether linkage at a selected position of its phenyl ring. The immunogen of the present invention, comprising the haptenic drug covalently linked through an ether linkage on the phenyl ring to an immunogenic carrier material, stimulates the production of antibodies to the drug. By coupling the drug on the phenyl ring where no substituents appear in the parent drug, the immunogen conjugate is prepared without modifying any functional or distinguishing groups on the drug.

In a preferred embodiment, the present invention provides novel intermediates in the preparation of the phenyl-substituted disopyramide reagents. Also provided are an improved immunoassay method and reagent system for the determination of the drug with the use of the novel antibodies of the present invention. The present invention also provides labeled disopyramide conjugates for particularly preferred embodiments of such immunoassay.

DESCRIPTION OF THE PREFERRED EMBODIMENTS

The present invention, in all of its interrelated embodiments, is focused on preparation of phenyl-substituted disopyramide derivatives which can then be used to form immunogens by coupling them to conventional carrier materials, and subsequently used to obtain disopyramide antibodies, or can be used to form labeled conjugates which serve as the detection reagents in disopyramide immunoassays. In particular, disopyramide is substituted at a selected position, preferably the para-position, of the phenyl ring through an ether linkage. The synthesis of such derivatives of disopyramide is based on that for the known 4-methoxy analog [A. Karim, et al, *J. Pharm. Sci.* 61: 888 (1972)].

Phenyl-Derivatives

The key starting material is an alkoxy-substituted derivative (A) of phenylacetonitrile:

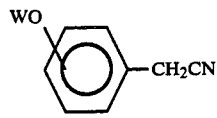
(A)

wherein W is a phenolic OH protecting group which can be removed later in the synthetic sequence, e.g., methyl, benzyl, substituted benzyl, and so forth [see "Protecting Groups in Organic Synthesis", T. W. Green, Wiley and Sons (New York 1981) pp. 87 et seq]. In order to obtain the desired ortho-, meta-, or para-substituted disopyramide derivative, one simply selects the correspondingly substituted phenylacetonitrile (A). ortho-Hydroxyphenylacetonitrile is made by the method of K. Anwers, *Ber.* 40: 3506 (1907); the meta-isomer is prepared according to T. Kametani et al, *Yakugaku Zasshi* 89: 1483 (1969), *Chem. Abst.* 72: 55212m (1970); and the para-isomer is commercially available (Aldrich Chemical Co., Milwaukee, WI, USA).

Alkylation of (A) with 2-bromopyridine gives nitrile intermediate (B):

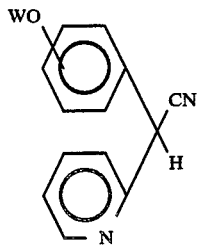
(B)

which upon stepwise alkylation with diisopropylaminoethyl chloride, hydrolysis of the nitrile function with base (e.g., potassium hydroxide), and removal of the protecting group W yields the hydroxy-derivative of disopyramide (C):

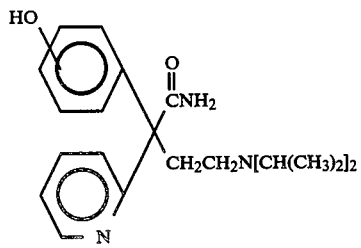
(C)

wherein the hydroxyl group occupies a singular position on the phenyl ring. Such derivatives can then be converted to a desired functionalized derivative (D) by alkylation with the reagent Z-R'-X where X is an appropriate leaving group such as chloro, bromo, iodo, p-toluensesulfonyl, methanesulfonyl, and the like:

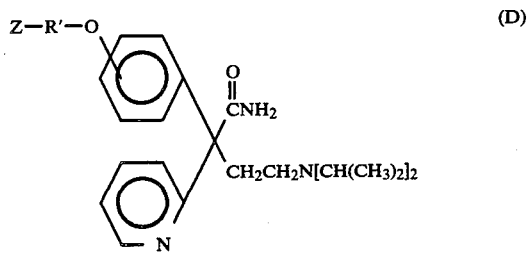
(D)

with Z representing a functional group capable of being coupled to immunogenic carrier materials or labeling reagents and wherein R' is an appropriate bridging group depending on the specific structure of the selected alkylating agent Z-R'-X. Functional group Z commonly is amino, carboxyl, thiol, hydroxyl, or maleimido, or a protected form or precursor thereof. The only critical feature of the reagent Z-R'-X is that leaving group X be attached to R' in such a way that it will undergo a typical nucleophilic displacement upon reaction with the phenolic hydroxyl of the disopyramide derivative (C). Examples of alkylating reagents Z-R'-X are those comprising elements selected from any combination of the following:

| Z | R' | X |
|---|---|---|
| $CF_3CONH-$ | $-(CH_2)_{\overline{n}}$ | $CH_3SO_3$ |
| $C_2H_5OOC-$ | ⬡$-CH_2-$ $(CH_2)_{\overline{3}}$ | $CH_3-$⬡$-SO_3$ |
| $CH_3COO-$ | $-CH_2CH=CHCH_2-$ | Cl |
| phthalimido | $-(CH_2)_{\overline{2}}-O-(CH_2)_{\overline{2}}-$ | Br |

It is evident that one skilled in the art has a wide variety of linking groups R' that can be introduced into the derivatives of the present invention. Exemplary of such choices are linear and branched alkylenes comprising from 1 to as many as 15, more usually 10 or less, and normally less than 6, carbon atoms (e.g., methylene, ethylene, n-propylene, iso-propylene, n-butylene, and so forth). In addition, such alkylenes can contain other substituent groups such as cyano, amino, (including substituted amino), acylamino, halogen, thiol, hydroxyl, carbonyl groups, carboxyl (including substituted carboxyls such as esters, amides, and substituted amides), providing, of course, that any such functional group not interfere with the subsequent synthetic steps, particularly the coupling to carrier materials or labeling reagents. The linking group R' can also contain or consist of substituted or unsubstituted aryl, aralkyl, or heteroaryl groups (e.g., phenylene, phenethylene, and so forth). Additionally, such linkages can contain one or more heteroatoms selected from nitrogen, sulfur and oxygen in the form of ether, ester, amido, thio ether, amidino, sulfone, or sulfoxide. Also, such linkages can include unsaturated groupings such as olefinic or acetylenic bonds, imino, or oximino groups. Preferably R' will be a chain, usually an aliphatic group, comprising between 1 and 20 atoms, more usually between 1 and 10, excluding hydrogen, of which between 0 and 5 are heteroatoms selected from nitrogen, oxygen, and sulfur. Particularly preferred are the derivatives wherein R' is —(CH$_2$)$_n$— with n being an integer from 1 through 10 and wherein Z is amino or carboxyl, or a protected form thereof. Therefore, the choice of linking group R' is not critical to the present invention and may be selected by one of ordinary skill taking normal precautions to assure that stable compounds are produced.

Examples of synthetic routes available to obtain phenyl-substituted disopyramide derivatives having such linking groups R' and terminal functional groups Z follow.

Following the procedure outlined above, derivative (C) can be alkylated with omega-bromoalkyl phthalimides to give derivatives (D) where R' is —(CH$_2$)$_n$— and Z is phthalimido, a protected form of NH$_2$, which can be converted to NH$_2$ by reaction with hydrazine. Such bromo-phthalimides where n is 2–4 are commercially available. Analogs n=5–9 are known compounds [cf. Dirscher and Weingarten, *Ann.* 574: 131 (1951); Muller and Krauss, *Montash.* 61: 219 (1932); Elderfield et al, *J. Am. Chem. Soc.* 68: 1568 (1946); Donahue et al. *J. Org. Chem.* 22: 68 (1957)].

Derivatives (C) can also be alkylated with omega-bromoalkanoic acid esters to give derivatives (D) where R' is —(CH$_2$)$_n$— and Z is —COOC$_2$H$_5$, a precursor of —COOH. Ethyl omega-bromoesters where n=1 through 4 are commercially available; n=5 through 9 are known compounds [cf. Barger, et al, *J. Chem. Soc.* (1937), 714; Salmon-Legagneur, *Bull. Soc. Chem. France*, (1956), 411; Linnell and Vora, *J. Pharm. Pharmacol.* 4: 55 (1952)].

In addition, derivatives (C) can be alkylated with omega-haloalkanals which are available from the class of omega-hydroxyaldehydes [Hurd, et al, *J. Am Chem. Soc.* 74: 5324 (1952)], to give derivatives (D) having R'=—(CH$_2$)$_n$— and Z=CHO.

Examples of derivatives (D) where Z is thiol can be obtained by reacting Z=NH$_2$ with N-succinimidyl 3-(2-pyridyldithio)propionate and reducing the product, usually in situ, to the free thiol compound [cf. Carlsson, et al, *Biochem. J.* 173: 723 (1978)].

Disopyramide compounds functionalized with maleimido groups can be prepared by reacting the corresponding amino-derivative (C), Z=NH$_2$, with maleic anhydride and cyclizing the product to form the maleimido group. Alternatively, amino derivatives of the drug can be reacted with maleimido-substituted carboxylic acids to give maleimido-substituted disopyramides in which the original linking group R' present in the amines has been extended to include the amide function contributed by the maleimido carboxylic acid. Examples of the latter are known [Kitagawa and Aikawa, *J. Biochem.* 79: 233 (1976); Keller and Riedinger, *Helv. Chim. Acta* 58: 531 (1975)].

Similarly, the linking group R' can vary widely. For example, a disopyramide derivative (D) containing an unsaturated linkage can be synthesized by reacting derivative (C) with N-(4-bromobutenyl)phthalimide [L. Birkofer and K. Hempel, *Chem. Ber.* 93: 2282 (1960)].

A phenylene linking group can be introduced by alkylating derivatives (C) with 2-(3-chloropropyl)benzyl chloride to give derivatives (D) wherein

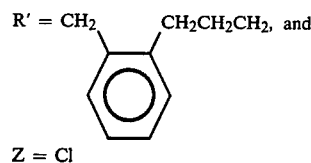

which can be further transformed to the carboxyl derivative, Z=COOH, by reaction with cyanide ion and treatment with acid [cf. Buckler, et al, *Europ. J. Med. Chem.* 12: 463 (1977)].

From the above-described synthetic routes, it is clear that phenyl-substituted oxy-derivatives of disopyramide of general structure (D), where Z is a reactive group for coupling to an immunogenic carrier material or an appropriate labeling residue, can be prepared with a wide latitude in the nature of linking group R'.

Immunogens

The above-described phenyl-substituted oxy-derivatives of disopyramide can be covalently linked by any number of conventional techniques to immunogenic carrier materials to yield immunogens comprising one or more residues of the formula:

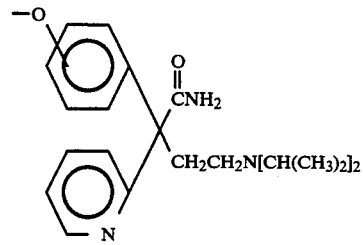

More particularly, such immunogens will have the formula:

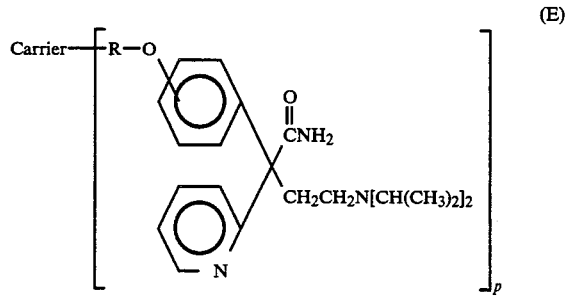

(E)

wherein Carrier is an immunogenic carrier material, R is an appropriate linking group and p is the number of hapten moieties coupled to the carrier. The number p is sometimes referred to as the epitopic density of the immunogen and is limited only by the number of available coupling sites on the carrier molecule. However, in the usual situation where the carrier is a naturally occurring protein such as albumin, R will be on the average from 1 to about 50, more normally from 1 to about 25. Optimal epitopic densities in such usual case, considering the ease and reproducibility of synthesis of the immunogen and antibody response, fall between about 2 and about 20, more usually between 5 and 15.

The immunogenic carrier material can be selected from any of those conventionally known. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 5,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins, having significant nonproteinaceous constituents, e.g., glycoproteins, and the like. The albumins and globulins of molecular weight between 30,000 and 200,000 are particularly preferred. Further reference for the state-of-the-art concerning conventional immunogenic carrier materials and techniques for coupling haptens thereto may be had to the following: Parker, *Radioimmunoassay of Biologically Active Compounds*, Prentice-Hall (Englewood Cliffs, N.J. USA, 1976); Butler, *J. Immunol. Meth.* 7: 1–24 (1975); Weinryb and Shroff, *Drug Metab. Rev.* 10: 271–238 (1975); Broughton and Strong, *Clin. Chem.* 22: 726–732 (1976); and Playfair et al, *Br. Med. Bull.* 30: 24–31 (1974).

Appropriate phenyl-substituted disopyramide derivatives are couplable to immunogenic carrier materials according to well-known techniques. For example, amino derivatives can be coupled to carboxyl-bearing carriers (e.g., protein or polypeptide carriers) by common peptide bond-forming reactions by means of activated esters, acyl azide formation, carbodiimides, etc., see *Peptides*, ed. Goodman and Meinhofer, John Wiley & Sons (New York, 1977) p. 6 et seq, and *The Peptides, Analysis, Synthesis, Biology*, Vol. 1, Acadamic Press (New York 1979). The same methods apply likewise for attaching carboxylated derivatives to amino-bearing carriers.

Thiolated derivatives can be attached to thiol-containing polymers (IgG or thiolated proteins) by the disulfide exchange procedure [J. Martin, et al, *Biochem.* 20: 4229 (1981)]. Alternately, an amino-containing polymer can be reacted with the reagent MBS and the product coupled to thiol-containing derivatives by the process described by T. Kitagawa and T. Aikawa, *J. Biochem.* 79: 233 (1976). Maleimide derivatives can similarly be coupled to thiol-containing carriers [ibid]. Hydroxy derivatives can be attached to carriers using triichlorotriazine [G. Kay and E. M. Crook, *Nature* 216: 514 (1967)].

A multitude of other coupling techniques are available to those of ordinary skill in the art for joining the various derivatives of the present invention with conventional immunogenic carrier materials. For example, one skilled in the art can react an appropriate derivative with a bifunctional reagent such that one end thereof covalently couples with the derivative and the other end has a functional group for coupling to carriers as described above (e.g., amino, carboxyl, thiol, hydroxyl, and maleimido). For example, bifunctional coupling reagents are well known for coupling amine derivatives to amino-containing carriers (e.g., protein or polypeptide carriers) by toluene-2,4-diisocyanate [Hirs and Timasheff, *Methods in Enzymol.* 25 (Part B): 625 (1972)]; 4,4′-difluoro-3,3--dinitrodiphenyl sulfone [P. S. Cuatrecasas, et al, *J. Biol. Chem.* 244: 406 (1969)]; glutaraldehyde [L. A. Frohman, et al, *Endocrinol.* 87: 1055 (1970)]; bis-imidates [A. Dutton, et al, *Biochem. Biophys. Res. Comm.* 23: 730)1966)]; and chlorotriazine [Kay and Crook, ;i Nature 216: 514 (1967)]. Other useful coupling reactions are thoroughly discussed in the literature [see Kopple, *Peptides and Amino Acids*, W. A. Benjamin, Inc. (New York 1966); Lowe and Dean, *Affinity Chromatography*, John Wiley & Sons (New York 1974); Means and Feeney, *Chemical Modification of Proteins*, Holden-Day (San Francisco 1971); and Glazer et al, *Chemical Modification of Proteins*, Holden-Day (San Francisco 1971); and Glazer et al, *Chemical Modification of Proteins*, Elsevier (New York 1975)].

In formula (E) depicting the present disopyramide immunogens, linking group R will comprise the residue —Z′—R′— where Z′ is the residue of functional group Z remaining after the coupling reaction and R′ is as described above. As previously detailed, residue Z′ may be linked directly by a bond to an appropriate functional group on the carrier or may be linked through the residue of a bifunctional coupling reagent. Thus, as in the case of R′, linking group R will vary widely and its exact chemical structure is not critical so long as it serves the purpose of linking the hapten residue without interfering with the immunogenic properties of the resulting immunogen. In particular, linking group R can be characterized by the same diversity of structure as described above for R′. Residue Z′ will vary according to the functional group Z in the disopyramide derivative (D) used, and preferably will be imino, carboxyl, sulfo, or oxy.

Particularly preferred are the immunogens of the formula:

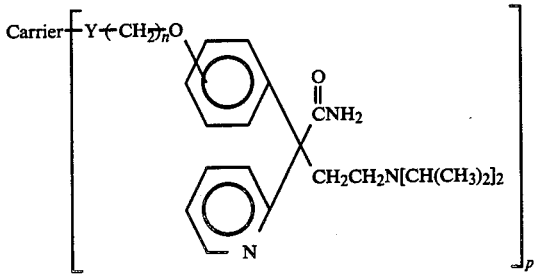

wherein Carrier is an immunogenic protein or polypeptide, Y is an amide group, i.e., —NHCO—, n is an integer from 1 through 10, preferably from 1 through 6, and p is on the average from 1 to the number of available amide coupling sites on the carrier material and preferably is as defined above. The amide coupling group can be oriented in either of the two possible ways, with the nitrogen atom in the amide group being from carrier amino groups and the carbon atom being from an appropriate derivative (e.g., a carboxylic acid), with p then representing the average number of coupled amino groups in the carrier (and preferably is as defined above), or with the nitrogen atom being from an appropriate derivative (e.g., an amino derivative) and the carbon atom being from carrier carboxyl groups, with p then representing the average number of coupled carboxyl groups in the carrier (and preferably is again as defined above).

Antibodies

Preparation of specific antibodies using the present immunogen conjugates may follow any conventional technique. Numerous texts are available describing the fundamental aspects of inducing antibody formation, for example reference may be made to Parker, *Radioimmunoassay of Biologically Active Compounds*, Prentice-Hall (Englewood Cliffs, N.J., USA. (1976). In the usual case, a host animal such as a rabbit, goat, mouse, guinea pig, or horse is injected at one or more of a variety of sites with the immunogen conjugate, normally in mixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps may be taken to remove undesired material such as nonspecific antibodies before the antiserum is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas*, ed. Melchers et al, Springer-Verlag (New York 1978), *Nature* 266: 495 (1977), *Science* 208: 692 (1980), and *Methods in Enzymology* 63 (Part B): 3–46(1981).

Immunoassay Techniques

The antibodies prepared from the immunogens of the present invention can be used in any immunoassay method, and the corresponding reagent system, for determining disopyramide, including agglutination techniques, radioimmunoassays, heterogeneous enzyme immunoassays (cf. U.S. Pat. No. 3,654,090), heterogeneous fluorescent immunoassays (cf. U.S. Pat. Nos., 4,201,763; 4,171,311; 4,133,639 and 3,992,631), and homogeneous (separation-free) immunoassays. The lattermost are particularly preferred and include such techniques as fluorescence quenching or enhancement (cf. U.S. Pat. No. 4,160,016), fluorescence polarization (cf. *J. Exp. Med.* 122: 1029 (1965), enzyme substrate-labeled immunoassay (cf. U.S. Pat. No. 4,279,992 and U.K. Pat. Spec. No. 1,552,607), prosthetic group-labeled immunoassay (cf. U.S. Pat. No. 4,238,565), enzyme modulator-labeled immunoassay, e.g., using inhibitor labels (cf. U.S. Pat. Nos. 4,134,792 and 4,273,866), enzyme-labeled immunoassay (cf. U.S. Pat. No. 3,817,837), energy transfer immunoassay (cf. U.S. Pat. No. 3,996,345), and double antibody steric hindrance immunoassay (cf. U.S. Pat. Nos. 3,935,074 and 3,998,943). Homogeneous immunoassays, as is known in the art, are typically performed by setting up competition between the analyte and the labeled conjugate of the drug for binding to antibody and are characterized by the fact that the detectable label property is altered when the labeled conjugate is bound by antibody.

Moreover, the disopyramide derivatives (D) of the present invention can be used to prepare the labeled conjugates needed to perform the various immunoassays described above. Appropriate derivatives can be radio-labeled or labeled with fluorescent moieties in accordance with standard methods. Likewise the appropriate labeling moiety for the preferred homogeneous techniques, e.g., an enzyme substrate, a prosthetic group, an enzyme modulator, or an enzyme (which is a protein and can be coupled similarly to the immunogenic carrier as described above) can be coupled to the derivatives to yield labeled conjugates.

Particularly preferred labeled conjugates are the β-galactosyl-umbelliferone-disopyramide conjugates of the formula:

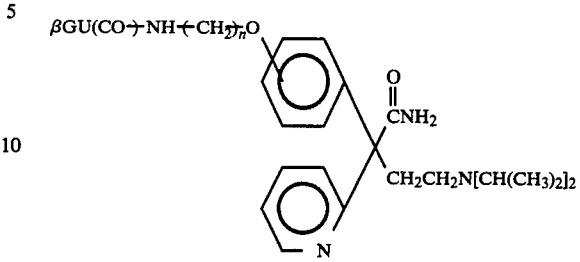

wherein βGU(CO) is

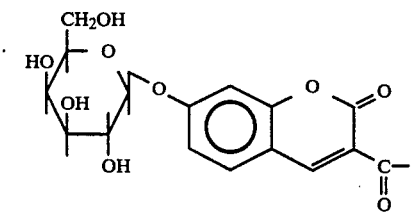

and n is an integer from 1 through 10. Such conjugates are prepared by standard peptide condensations of β-galactosyl-umbelliferone carboxylic acid (U.S. Pat. No. 4,226,978) with the appropriate amino-derivative of disopyramide.

The reagent system or means of the present invention comprises all of the essential chemical elements required to conduct a desired disopyramide immunoassay method encompassed by the present invention. The reagent system is presented in a commercially packaged form, as a composition or admixture where the compatibility of the reagents will allow, in a test device configuration, or as a test kit, i.e., a packaged combination of one or more containers holding the necessary reagents. Included in the reagent system are the reagents appropriate for the binding reaction system desired, e.g., an antibody and labeled conjugate of the present invention. Of course, the reagent system can include other materials as are known in the art and which may be desirable from a commercial and user standpoint, such as buffers, diluents, standards, and so forth. Particularly preferred is a test kit for the homogeneous competitive binding immunoassay of the present invention comprising (a) a disopyramide antibody of the present invention and (b) a labeled disopyramide conjugate which has a detectable property which is altered when bound with the antibody. Also preferred is a test device comprising a reagent composition including a disopyramide antibody of the present invention and a labeled disopyramide conjugate which has a detectable property which is altered when bound with the antibody, and a solid carrier member incorporated with the reagent composition. The various forms of such test device are described in U.S. patent application Ser. No. 202,378, filed Oct. 30, 1980, which is incorporated herein by reference and which has published as European patent application No. 51,213. The specific label used in the preferred test kit and test device will depend on the technique followed, as described hereinabove.

The present invention will now be illustrated, but is not intended to be limited, by the following examples:

EXAMPLES

Reagents

α-[2-(Diisopropylamino)ethyl]-α-(4-hydroxyphenyl)-2-pyridineacetamide

A solution of 7.32 grams (g) [0.02 moles (mol)] of α-[2-(diisopropylamino)ethyl]-α-(4-methoxyphenyl)-2-pyridineacetamide [Karim, supra] in 250 milliliters (mL) of methylene chloride ($CH_2Cl_2$) was cooled to $-78°$ C. while stirring under an inert atmosphere. To this was added dropwise 19.85 g (0.08 mol) of boron tribromide dissolved in 50 mL of $CH_2Cl_2$. The resulting brown suspension was allowed to warm to room temperature, then was heated at reflux for 1 hour. It was cooled to $-10°$ C., and excess boron tribromide destroyed by the addition of 150 mL of 10% sodium hydroxide (NaOH) solution. The organic phase was separated and extracted with n-butanol. Evaporation left a residue which was purified by chromatography on silica gel eluting with 60:10:1 (v/v/v) $CHCl_3$:MeOH:conc. ammonium hydroxide. This gave 4.8 g of the phenol as a pale tan solid. A sample was recrystallized from toluene to give a solid, mp 148°–151° C.

Analysis: Calculated for $C_{21}H_{29}N_3O_2$: C, 70.96; H, 8.22; N, 11.82. Found: C, 61.02; H, 8.26; N, 11.69.

α-[2-(Diisopropylamino)ethyl]-α-[4-(6-N-phthalimidohexoxy)phenyl]-2-pyridineacetamide The preceeding phenol (5.3 g, 15 mmol) was combined with 360 mg (15 mmol) of sodium hydride in 100 mL of dry dimethylformamide (DMF). When gas evolution ceased, a solution of 4.65 g (15 mmol) of N-(6-bromohexyl)phthalimide in 100 mL of DMF was added. After 16 hours at room temperature, solvent was removed under reduced pressure. The oily residue was taken up in $CHCl_3$, washed with $H_2O$, dried and evaporated. The residue was purified by chromatography on silica gel eluting with 60:10:1 (v/v/v) chloroform ($CHCl_3$):methanol (MeOH):conc. ammonium hydroxide ($NH_4OH$) and yielded the phthalimido derivative as 3.4 g of a brown oil.

α-[2-(Diisopropylamino)ethyl]-α-[4-(6-aminohexoxy)phenyl]-2-pyridineacetamide

The preceeding phthalimide was refluxed for 4 hours in a solution of 30 mL of ethanol containing 1 equivalent of hydrazine. Solvent was evaporated and the residue purified by chromatography on silica gel eluting with 60:10:1 (v/v/v) $CHCl_3$:MeOH:conc. $NH_4OH$. This yielded 800 mg of the desired amine as an oil.

Analysis: Calculated for $C_{27}H_{42}H_4O_2$: C, 71.41; H, 9.31; N, 12.32. Found: C, 72.03; H, 8.93; N, 11.72.

B. Preparation of labeled conjugate

N-[6-[4-[1-Aminocarbonyl-3-diisopropylamino-1-(2-pyridyl)propyl]phenoxy]hexyl]-7-β-galactosylcoumarin-3-carboxamide A suspension of 420 milligrams (mg) [(1.05 millimoles (mmol)] of 7-β-galactosylcoumarin-3-carboxylic acid [U.S. Pat. No. 4,226,978] in 14 mL of dry dimethylformamide (DMF) was stirred at 0° C. and to it was added 120 mg (1.05 mol) of N-hydroxysuccinimide and 210 mg (1.01 mmol) of dicyclohexylcarbodiimide. The reaction was allowed to warm to room temperature and stir for 2 hours. It was then filtered to remove precipitated dicyclohexylurea and the filtrate added dropwise to a 0° C. solution of 400 mg (0.88 mmol) of the amine in 10 mL of DMF containing 2 equivalents of triethylamine. After 1 hour, 5 g of silica gel was added and the solvent removed on a rotary evaporator attached to a vacuum pump. The impregnated adsorbent was placed atop a column of 100 g of silica gel and the column eluted with 6:1 (v/v) ethanol:1M triethylammonium bicarbonate. Fifteen mL fractions were collected. Fractions 15 to 50 were pooled and evaporated to give 500 mg of crude product. Purification was completed by chromatography on Sephadex LH-20 (Pharmacia Fine Chemicals, Uppsala, Sweden) eluting with MeOH. The label derivative of disopyramide was isolated as an amorphous solid.

Analysis: Calculated for $C_{43}H_{56}N_4O_{11}$: C, 64,16; H, 7.01; N, 6.96. Found: C, 63,61; H, 6.60; N, 6.76.

Mass Spectrum (FAB): m/e 805 [M+].

C. Preparation of Disopyramide Immunogen and Antibodies

Seventy-five (75) mg (0.167 mmol) of α-[(diisopyropylamino)ethyl]-α-[4-(6-aminohexoxy)-phenyl]-]-pyridineacetamide was dissolved in 2 mL of 1N HCl in a 10 mL serum vial with a small magnetic stir bar. The pH was adjusted to 4.5 with 0.1N NaOH. While stirring, 50 mg (0.70 μmole) of bovine serum albumin (BSA) was added. After the BSA was completely dissolved, the pH was readjusted to 4.5 with the dropwise addition of 0.1N HCl. With gentle stirring, 3.5 mg (1.65 mmole) of 1-ethyl-3-(3-dimethylaminopropyl)-carbodiimide hydrochloride (EDC) freshly dissolved in 1 mL of $H_2O$ was added dropwise to the mixture within one minute. The reaction mixture was transferred to an ice bath and kept stirring. The pH was adjusted to pH 5.5 with 0.1N HCl at hourly intervals for three hours before being placed in a 4° C. cold room overnight. The next morning the reaction mixture was brought to room temperature prior to application to a Sephadex G-25 column (Pharmacia Fine Chemicals).

The reaction mixture was applied to a column (1.5×30 cm) of Sephadex G-25 preequilibrated with phosphate-buffered saline (PBS) pH 7.4. Two mL fractions were monitored for absorbance at 280 nm. The immunogen was eluted with PBS in the void volume and these column fractions (12–18) were pooled. The pool was placed in a dialysis bag and dialyzed against 5 liters (L) of PBS, pH 7.3 (4 changes) for 48 hours at 4° C. The protein concentration of the immunogen was then determined by an appropriate method [e.g., Lowry et al, *J. Biol. Chem.* 193: 265 (1957)] and diluted to 1 mg/mL with saline (0.85% NaCl).

Six mL of immunogen (1 mg/mL) was combined with 12 mL of Fruends complete adjuvant and 6 mL of saline. Rabbits were immunized simultaneously each with 2 mL of this mixture. Three weeks later they were reimmunized with the same mixture prepared with incomplete Fruends adjuvant. The booster immunizations were repeated every four weeks. Test bleedings were taken one week after the boosters. Antiserum with suitable titers were obtained by three months after the initial immunizations.

Immunoassay

A homogeneous substrate-labeled fluorescent immunoassay (SLFIA-U.S. Pat. No. 4,279,992) for disopyramide was established as follows:

A. Reagents

1. Antibody/Enzyme Reagent-50 mM Bicine [N,N-bis-(2-hydroxyethyl)glycine, Calbiochem-Behring Corp., LaJolla, CA], pH. 8.3 containing 0.11 units/mL β-galactosidase, sufficient antiserum raised against the disopyramide immunogen to decrease fluorescence to 24% of that in the absence of antiserum, and 15.4 mM sodium azide.
2. Conjugate Reagent-30 mM formate buffer, pH 3.5, containing 0.01% (v/v) Tween 20 detergent (Fisher Scientific, Fairlawn, NJ, USA), and 0.008 $A_{343}$ units of β-GU-disopyramide.
3. Disopyramide Standards-USP reference standard disopyramide hydrochloride added to normal human serum; diluted 51-fold with 50 mM Bicine buffer, containing 15.4 mM sodium azide.

B. Inhibition of Hydrolysis of β-GU-Disopyramide by Antiserum to Disopyramide Increasing amounts of antiserum were added to 1.5 mL of Bicine buffer containing 0.11 units/mL β-galactosidase. The reactions were initiated with 50 microliters (μL) of the Conjugate Reagent added to each cuvette with mixing. After 20 minutes the fluorescence intensity was measured in each cuvette (excitation 400 nm, emission 450 nm). The results are presented in Table 1.

TABLE 1

| μL Antiserum | Fluorescence |
| --- | --- |
| 0 | 2.90 |
| 1 | 1.82 |
| 2 | 1.03 |
| 4 | 0.44 |
| 8 | 0.27 |

C. Assay Method and Results

To 1.5 mL of the Antibody/Enzyme Reagent in cuvettes were added 50 μL of the diluted disopyramide standards. Then to begin the reaction, 50 μL of the Conjugate Reagent was added to each cuvette with mixing. After 20 minutes the fluorescence intensity was measured in each cuvette (excitation 400 nm, emission 450 nm).

Performance of the assay yielded the results shown in Table 2.

TABLE 2

| μg/ml Disopyramide | Fluorescence |
| --- | --- |
| 0 | 2.3 |
| 2 | 3.6 |
| 4 | 4.9 |
| 6 | 5.9 |
| 8 | 6.8 |

This standard curve could be used to determine disopyramide in unknown serum samples.

What is claimed is:

1. A compound of the formula:

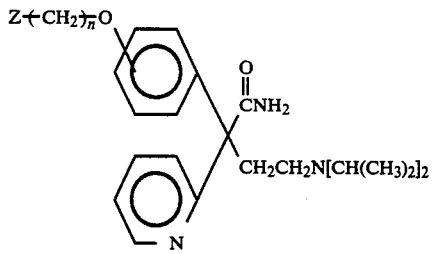

wherein Z is carboxyl or amino and n is an integer from 1 through 10.

2. The compound of claim 1 wherein the alkyleneoxy bridge group is connected to the phenyl ring at the para-position.
3. The compound of claim 2 wherein Z is amino.
4. The compound of claim 3 wherein n=6.
5. A β-galactosyl-umbelliferone-disopyramide conjugate of the formula:

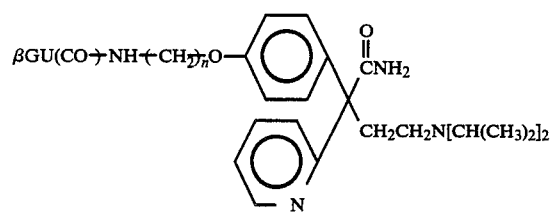

wherein βGU(CO— is

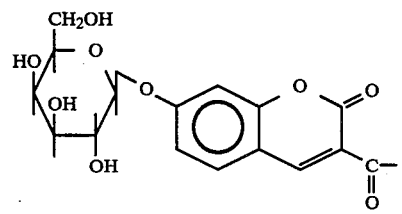

and n is an integer from 1 through 10.

6. The conjugate of claim 5 wherein n=6.

* * * * *